US010266771B2

(12) United States Patent
Kobilka et al.

(10) Patent No.: US 10,266,771 B2
(45) Date of Patent: *Apr. 23, 2019

(54) BONDABLE FLAME-RETARDANT VANILLIN-DERIVED MOLECULES

(71) Applicant: International Business Machines Corporation, Armonk, NY (US)

(72) Inventors: Brandon M. Kobilka, Tucson, AZ (US); Joseph Kuczynski, North Port, FL (US); Jacob T. Porter, Highland, NY (US); Jason T. Wertz, Pleasant Valley, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/584,753

(22) Filed: May 2, 2017

(65) Prior Publication Data

US 2018/0320073 A1    Nov. 8, 2018

(51) Int. Cl.
| | | |
|---|---|---|
| *C09K 21/12* | (2006.01) | |
| *C07F 9/08* | (2006.01) | |
| *C12P 7/22* | (2006.01) | |
| *C12P 7/26* | (2006.01) | |
| *C08K 5/5313* | (2006.01) | |
| *C08K 5/5317* | (2006.01) | |
| *C08K 5/5337* | (2006.01) | |

(52) U.S. Cl.
CPC ............. *C09K 21/12* (2013.01); *C07F 9/08* (2013.01); *C08K 5/5313* (2013.01); *C08K 5/5317* (2013.01); *C08K 5/5337* (2013.01); *C12P 7/22* (2013.01); *C12P 7/26* (2013.01)

(58) Field of Classification Search
CPC ......... C09K 21/12; C07F 9/08; C08K 5/5313; C08K 5/5317; C08K 5/5337; C12P 7/22; C12P 7/26
USPC .......................................................... 524/27
See application file for complete search history.

(56) References Cited

FOREIGN PATENT DOCUMENTS

| CN | 107011499 A | 8/2017 |
|---|---|---|
| JP | 2013185039 A | 9/2013 |
| WO | 2016172353 A1 | 10/2016 |
| WO | 2017007883 A1 | 1/2017 |

OTHER PUBLICATIONS

Fache et al., Green Chemistry, 18, 712-725, 2016.*
Kobilka et al., "Bondable Flame-Retardant Vanillin-Derived Molecules," U.S. Appl. No. 15/850,681, filed Dec. 21, 2017.
Kobilka et al., "Flame-Retardant Vanillin-Derived Cross-Linkers," U.S. Appl. No. 15/850,738, filed Dec. 21, 2017.
Kobilka et al., "Flame-Retardant Vanillin-Derived Monomers," U.S. Appl. No. 15/850,784, filed Dec. 21, 2017.
Kobilka et al., "Flame-Retardant Vanillin-Derived Small Molecules," U.S. Appl. No. 15/850,838, filed Dec. 21, 2017.
List of IBM Patents or Patent Applications Treated as Related, Signed Dec. 21, 2017, 2 pages.
Fache et al., "Epoxy thermosets from model mixtures of the lignin-to-vanillin process," Green Chemistry, 2016, 18, pp. 712-725, The Royal Society of Chemistry. DOI: 10.1039/c5gc01070e.
Fache et al., "Vanillin, a key-intermediate of biobased polymers," European Polymer Journal, 2015, vol. 68, pp. 488-502, Elsevier. DOI: 10.1016/j.eurpolymj.2015.03.050.
Fache et al., "Vanillin, a promising biobased building-block for monomer synthesis," Green Chemistry, 2014, 16, pp. 1987-1998, The Royal Society of Chemistry. DOI: 10.1039/c3gc42613k.
Illy et al., "Phosphorylation of bio-based compounds: the state of the art," Polymer Chemistry, 2015, 6 (35), pp. 6257-6291, The Royal Society of Chemistry DOI: 10.1039/c5py00812c.
Smolarski, N., "High-Value Opportunities for Lignin: Unlocking its Potential," Frost & Sullivan, Market Insight, Nov. 7, 2012, pp. 1-15.
Stanzione III, J., "S15.2. Vanillin: A Renewable and Versatile Platform Chemical for Sustainable Polymers," 14th International Symposium on Bioplastics, Biocomposites, and Biorefining, (May 31-Jun. 3, 2016), Jun. 22, 2016, pp. 1-26.
Kobilka et al., "Flame-Retardant Vanillin-Derived Cross-Linkers," U.S. Appl. No. 15/584,798, filed May 2017.
Kobilka et al., "Flame-Retardant Vanillin-Derived Monomers," U.S. Appl. No. 15/584,838, filed May 2, 2017.
Kobilka et al., "Flame-Retardant Vanillin-Derived Small Molecules," U.S. Appl. No. 15/584,866, filed May 2, 2017.
List of IBM Patents or Patent Applications Treated as Related, Signed May 2, 2017, 2 pages.

* cited by examiner

*Primary Examiner* — Hui H Chin
(74) *Attorney, Agent, or Firm* — Kelsey M. Skodje; Nathan M. Rau

(57) ABSTRACT

A flame-retardant vanillin-derived molecule, a process for forming a flame-retardant resin, and an article of manufacture comprising a material that contains the flame-retardant vanillin-derived molecule are disclosed. The flame-retardant vanillin-derived molecule can be synthesized from vanillin obtained from a bio-based source, and can have at least one phosphoryl or phosphonyl moiety with phenyl, allyl, epoxide, propylene carbonate, or thioether substituents. The process for forming the flame-retardant resin can include reacting a vanillin derivative and a flame-retardant phosphorus-based molecule to form the flame-retardant vanillin-derived molecule, and binding the flame-retardant vanillin-derived molecule to a resin. The flame-retardant vanillin-derived molecules can also be bound to polymers. The material in the article of manufacture can be flame-retardant, and contain the flame-retardant vanillin-derived molecules. Examples of materials that can be in the article of manufacture can include resins, plastics, adhesives, polymers, etc.

7 Claims, 15 Drawing Sheets

335 2-Mercaptoethanol

340 Cysteamine HCl 345 3-Mercaptopropionate

302

BONDABLE FLAME-RETARDANT VANILLIN-DERIVED MOLECULES

BACKGROUND

The present disclosure relates to bio-renewable flame-retardant compounds and, more specifically, resin-bondable flame-retardant vanillin-derived molecules.

Bio-based compounds provide a source of renewable materials for various industrial applications, such as polymers, flame retardants, cross-linkers, etc. One example of a bio-based compound that can be used in these applications is vanillin (4-hydroxy-3-methoxybenzaldehyde). Vanillin is a plant metabolite and the main component of natural vanilla extract. While vanillin can be obtained from vanilla extract, or synthesized from petroleum-based raw materials, a number of biotechnology processes are also used to produce vanillin. These processes can be plant-based or microorganism-based, and provide a renewable source of vanillin on an industrial scale.

SUMMARY

Various embodiments are directed to flame-retardant vanillin-derived molecules. The flame-retardant vanillin-derived molecules can have at least one phosphoryl or phosphonyl moiety. Each phosphoryl or phosphonyl moiety can have at least one substituent selected from a group consisting of a phenyl substituent, an allyl substituent, an epoxide substituent, a propylene carbonate substituent, and a thioether substituent. The thioether substituent can be a hydroxyl-functionalized thioether substituent, an amino-functionalized thioether substituent, or a carboxylic acid-functionalized thioether substituent. The flame-retardant vanillin-derived molecules can be synthesized from vanillin obtained from a bio-based source. Additional embodiments are directed to forming a flame-retardant resin. The resin can be produced by forming a vanillin derivative, forming a phosphorus-based flame-retardant molecule, and reacting the vanillin derivative and the phosphorus-based flame-retardant molecule with one another to form a flame-retardant vanillin-derived molecule. The flame-retardant vanillin-derived molecule can then be bound to a resin, forming the flame-retardant resin. The vanillin derivative can be a phenol vanillin derivative, a carboxylic acid vanillin derivative, or a benzyl alcohol vanillin derivative. The phosphorus-based flame-retardant molecule can be a phosphate-based molecule or a phosphonate-based molecule with at least one phenyl substituent, allyl substituent, epoxide substituent, propylene carbonate substituent, or thioether substituent. Further embodiments are directed to an article of manufacture comprising a material that contains the flame-retardant vanillin-derived molecule. The material can be a resin, plastic, adhesive, polymer, etc. Examples of polymer materials can include polyurethane, an epoxy, a polyhydroxyurethane, a polycarbonate, a polyester, a polyacrylate, a polyimide, a polyamide, a polyurea, and a poly(vinyl-ester).

DETAILED DESCRIPTION

Bio-based compounds are increasingly being used in the synthesis of substances that previously required petroleum-based raw materials. One benefit of bio-based compounds is that they are from renewable resources. Therefore, these compounds have applications in sustainable, or "green," materials. Sustainable materials are becoming more and more prevalent, due to the rising costs of fossil fuels and increasing environmental regulatory controls. Advances in biotechnology have provided numerous strategies for efficiently and inexpensively producing bio-based compounds on an industrial scale. Examples of these strategies include plant-based or microorganism-based approaches. Plant-based approaches can involve obtaining a material directly from a plant, or growing plant tissues or cells that can produce bio-based compounds from various substrates using their own biosynthetic pathways. Microorganism-based approaches involve using native or genetically modified fungi, yeast, or bacteria to produce a desired compound from a structurally similar substrate.

Examples of substances that can be produced from bio-based compounds can include polymers, flame retardants, cross-linkers, etc. In some examples, bio-based polymers and petroleum-based polymers are blended to form a polymer composite. However, polymers can also be entirely bio-based, or produced from a combination of bio- and petroleum-based monomers. Bio-based compounds can also impart flame-retardant properties to bio- and petroleum-based polymers. For example, flame-retardant monomers or cross-linkers can be incorporated into polymers. Additionally, flame-retardant molecules can be blended or chemically reacted with the polymers.

Vanillin (4-hydroxy-3-methoxybenzaldehyde) is one example of a bio-based compound that has applications as a component of various polymers, resins, and small molecules. Vanillin is a plant metabolite and the main component of natural vanilla extract. It can be obtained from the plant- and microorganism-based bio-sources discussed above, or synthesized from petroleum-based raw materials. According to some embodiments of the present disclosure, vanillin is used as a precursor for flame-retardant molecules. These flame-retardant vanillin-derived molecules can be bound to polymers and resins by functional groups on flame-retardant moieties.

Figure 1:
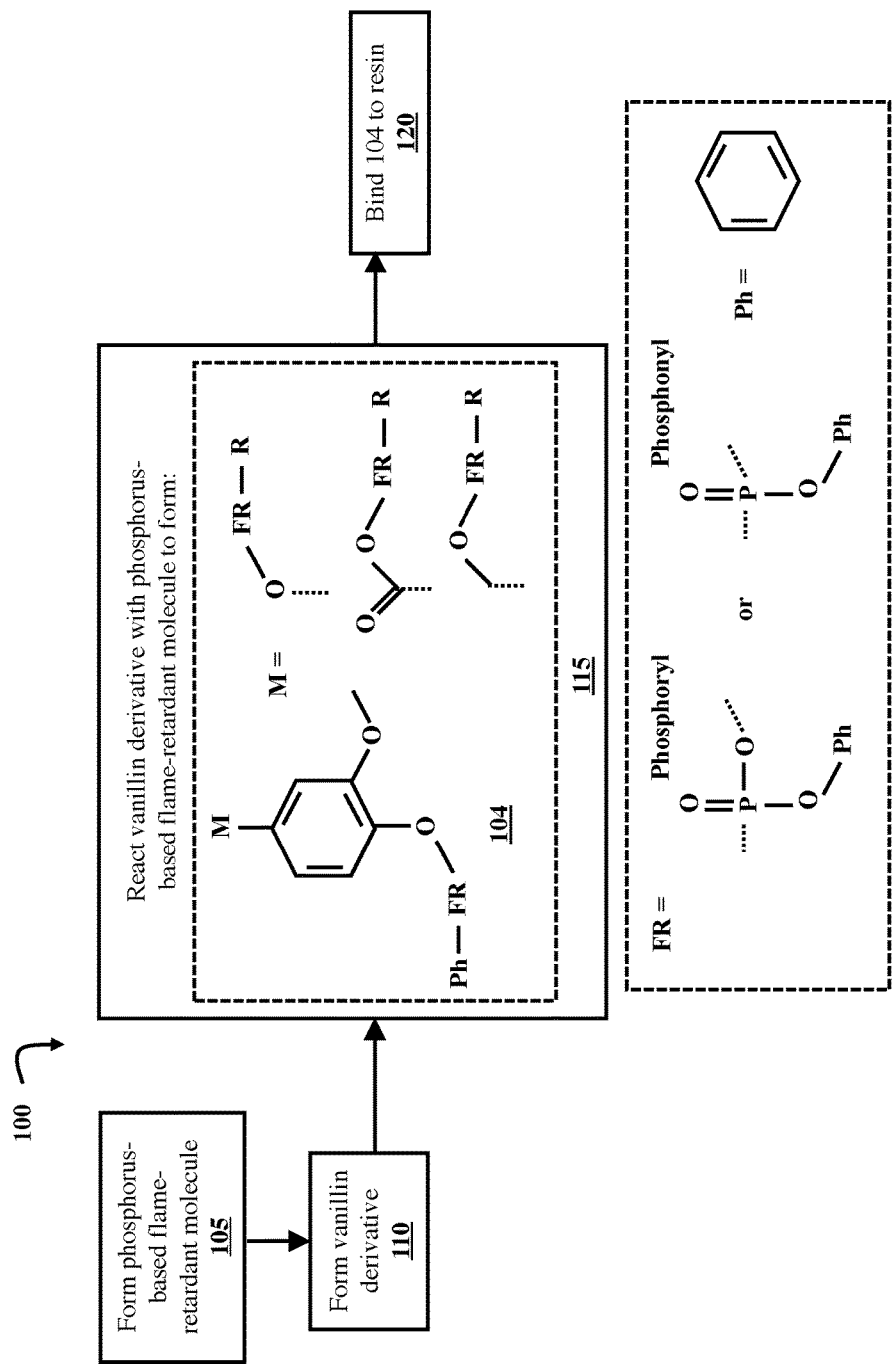
FIG. 1 is a flow diagram illustrating a process of forming a flame-retardant polymer containing a flame-retardant vanillin-derived molecule, according to embodiments of the present disclosure.

FIG. 1 is a flow diagram 100 illustrating a process of forming a flame-retardant polymer containing a flame-retardant vanillin-derived molecule 104, according to embodiments of the present disclosure. Process 100 begins with the formation of a phosphorus-based flame-retardant molecule. This is illustrated at step 105. The phosphorus-based flame-retardant molecule has either a phosphoryl or a phosphonyl moiety (collectively referred to as an FR group) with an attached R group. Examples of R groups that can be attached to the FR group can include phenyl substituents, epoxide substituents, allyl substituents, propylene carbonate substituents, hydroxyl-functionalized thioether substituents, amino-functionalized thioether substituents, and carboxylic acid-functionalized thioether substituents. The syntheses and structures of phosphorus-based flame-retardant molecules are discussed in greater detail with regard to FIGS. 2B-3B.

Process 100 continues with the formation of a flame-retardant vanillin derivative. This is illustrated at step 110. Each vanillin derivative has a flame-retardant group and a hydroxyl group. The derivatives are formed by a reaction of vanillin with the phosphorus-based flame-retardant molecule and a reaction that replaces vanillin's aldehyde functional group with a hydroxyl group. Examples of reactions that can convert the aldehyde group to a hydroxyl group can include oxidation by sodium percarbonate, oxidation by potassium permanganate, and reduction by sodium borohydride. The structures and syntheses of the derivatives of vanillin are discussed in greater detail with regard to FIG. 2A.

The vanillin derivative and the phosphorus-based flame-retardant molecule are chemically reacted in order to form a flame-retardant vanillin-derived molecule 104. This is illustrated at step 115. The identity of the M group on the flame-retardant vanillin-derived molecule 104 is determined by the phosphorus-based flame-retardant molecule and the vanillin derivative used in the reaction. The phosphorus-based flame-retardant molecules react with hydroxyl groups on the vanillin derivatives synthesized in step 105 to provide the FR group with the attached R group. Examples of FR groups, as well as the syntheses and structures of flame-retardant vanillin-derived molecules 104 are discussed in greater detail with regard to FIGS. 4A-4I.

The flame-retardant vanillin-derived molecule 104 formed in step 115 is chemically reacted with a resin, forming a bond between the flame-retardant vanillin-derived molecules 104 and the resin. This is illustrated at step 120. The flame-retardant resins formed in step 120 can be converted into flame-retardant polymers. Examples of these polymers can include epoxies, polyhydroxyurethanes, polycarbonates, polyesters, polyacrylates, polyimides, polyamides, polyureas, poly(vinyl-esters), etc. The materials for these polymers can come from petroleum-based sources, bio-based sources, or a combination of petroleum- and bio-based sources. Further, in some embodiments, the flame-retardant vanillin-derived resin can be used in non-polymeric applications, such as varnishes and adhesives.

Figure 2A:
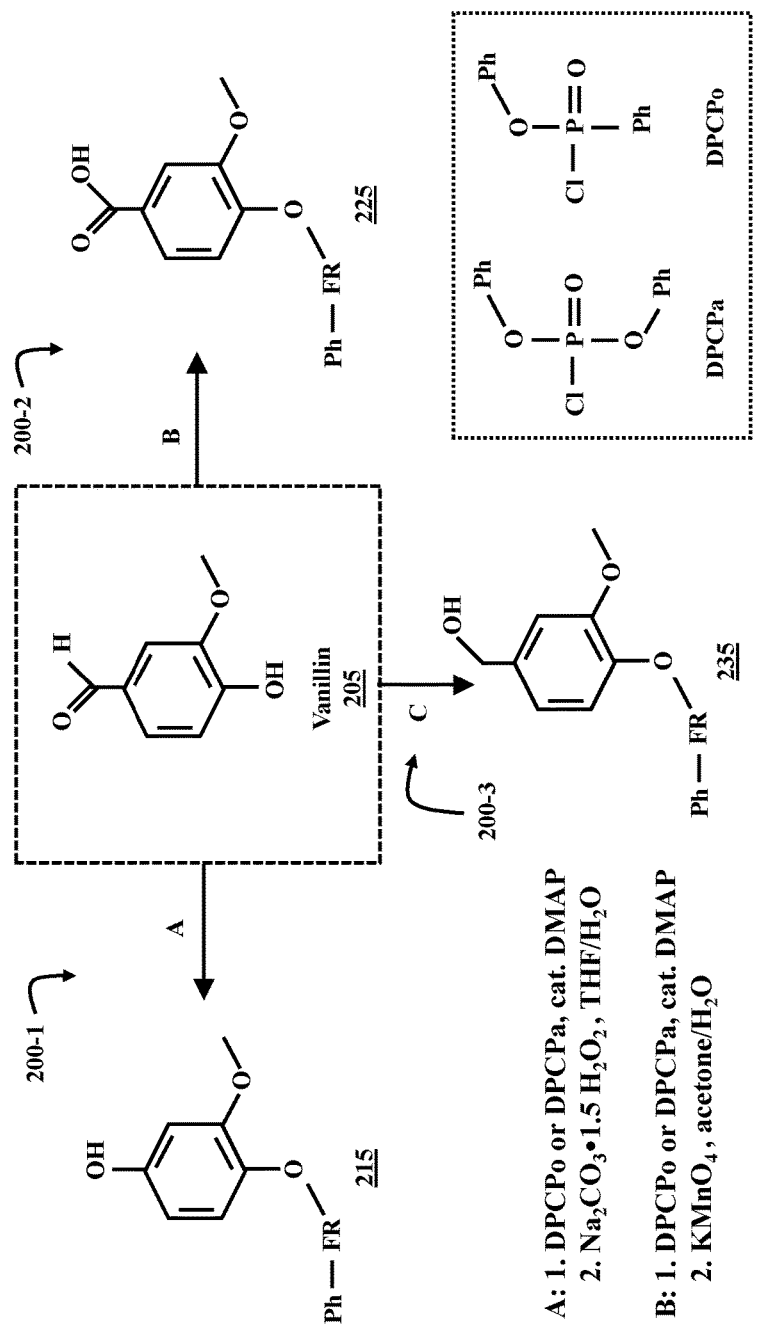
FIG. 2A is a chemical reaction diagram illustrating processes of synthesizing three flame-retardant vanillin derivatives, according to embodiments of the present disclosure.

FIG. 2A is a chemical reaction diagram illustrating processes 200-1, 200-2, and 200-3 of synthesizing three flame-retardant vanillin derivatives, according to embodiments of the present disclosure. The three vanillin derivatives are a phenol flame-retardant derivative 215, a carboxylic acid flame-retardant derivative 225, and a benzyl alcohol flame-retardant derivative 235. These vanillin derivatives are precursors for the flame-retardant vanillin-derived molecules 104, as described in greater detail with regard to FIGS. 4A, 4D, and 4G.

In process 200-1, the phenol flame-retardant derivative 215 of vanillin is produced. The first step in this reaction replaces vanillin's hydroxyl group with an FR group. The FR group is provided by a reaction between vanillin 205 and either diphenyl chlorophosphate (DPCPa) or diphenylphosphinic chloride (DPCPo), as well as catalytic dimethylaminopyridine (DMAP). If the reaction is carried out with DPCPa, the phenol flame-retardant derivative 215 will have phosphoryl FR substituents, and, if the reaction is carried out with DPCPo, the phenol flame-retardant derivative 215 will have phosphonyl FR substituents.

In the second step in process 200-1, deionized water ($H_2O$) and tetrahydrofuran (THF) are added to the reaction. The resulting mixture is degassed with an inert gas (e.g., argon or nitrogen). While agitating the mixture, sodium percarbonate ($Na_2CO_3.1.5H_2O_2$) is added until pH=3 is reached, thus quenching the reaction. After quenching the reaction, the THF is evaporated, and the aqueous phase is extracted with ethyl acetate. The organic phases are collected, washed with brine, and dried over anhydrous sodium sulfate ($Na_2SO_4$). The ethyl acetate is removed under reduced pressure, yielding the isolated phenol flame-retardant derivative 215.

In process 200-2, the carboxylic acid flame-retardant derivative 225 of vanillin is produced. The first step in this reaction replaces vanillin's hydroxyl group with an FR group, and is carried out under substantially the same conditions as the first step in process 200-1. In the second step, an acetone/$H_2O$ solution of potassium permanganate ($KMnO_4$) is added to the reaction. The mixture is stirred for approximately 1.5 hours at room temperature. A solution of sodium bisulfite ($NaHSO_3$) in hydrochloric acid (HCl) is added to the resulting purple mixture until the mixture is colorless. The mixture is extracted with ethyl acetate, and the organic phases are collected, washed with brine, and dried over anhydrous magnesium sulfate (MgSO$_4$). The ethyl acetate is removed under reduced pressure, yielding the isolated carboxylic acid flame-retardant derivative 225.

In process 200-3, the benzyl alcohol flame-retardant derivative 235 is produced. The first step in this reaction replaces vanillin's hydroxyl group with an FR group, and is carried out under substantially the same conditions as the first step in process 200-1. In the second step, sodium borohydride (NaBH$_4$) is added to a solution of vanillin 205 in anhydrous ether or tetrahydrofuran (THF). The mixture is stirred at room temperature under an inert gas (e.g., argon or nitrogen) for approximately four hours. The mixture is then concentrated, and purified by column chromatography to give the benzyl alcohol flame-retardant derivative 235.

Figure 2B:
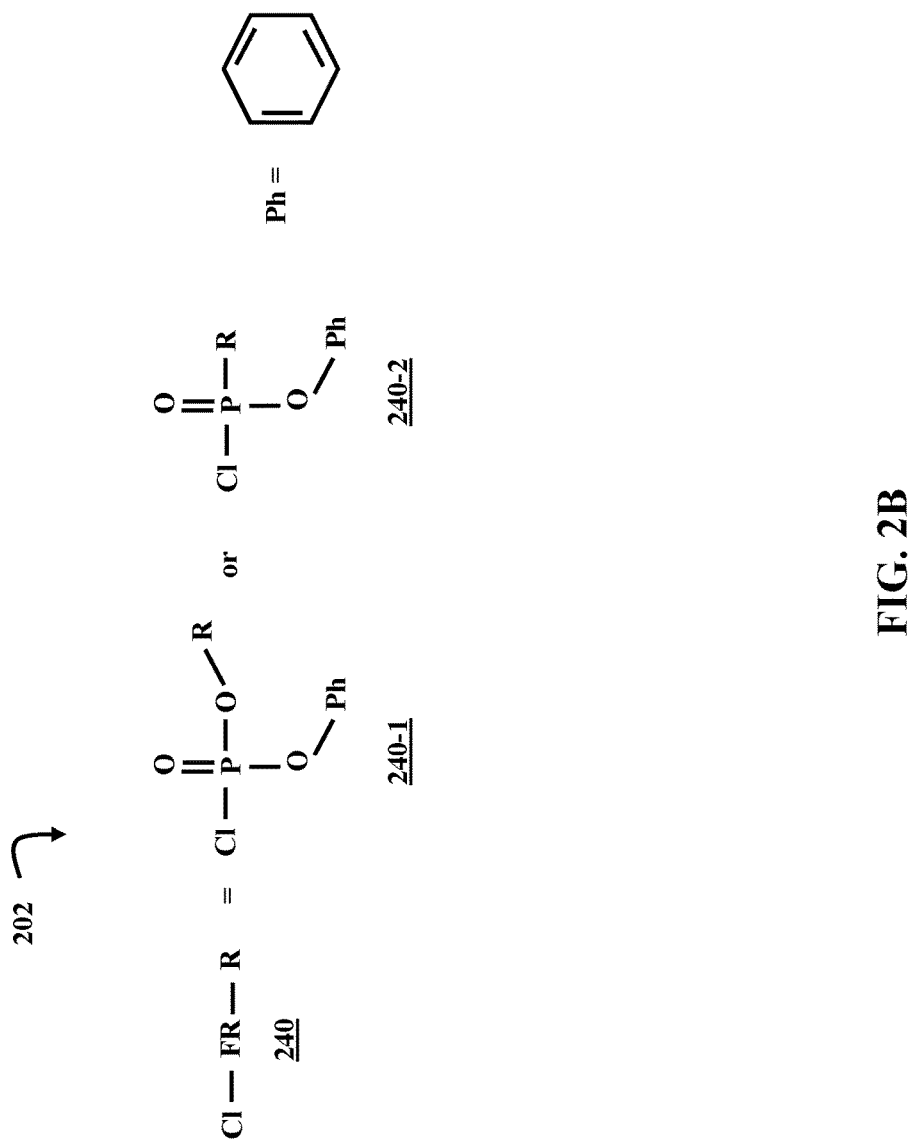
FIG. 2B is a diagrammatic representation of the molecular structures of generic phosphorus-based flame-retardant molecules, according to embodiments of the present disclosure.

FIG. 2B is a diagrammatic representation of the molecular structures 202 of generic phosphorus-based flame-retardant molecules 240, according to embodiments of the present disclosure. Each phosphorus-based flame-retardant molecule 240 is either a phosphate-based flame-retardant molecule 240-1 or a phosphonate-based flame-retardant molecule 240-2. Herein, phosphoryl and phosphonyl moieties are replaced by the abbreviation "FR" in order to simplify illustrations of the molecular structures. Each phosphorus-based flame-retardant molecule 240 has a phenyl (Ph) substituent and an R group that can bind to a resin.

The identities of the R groups bound to the phosphorus-based flame-retardant molecules 240 vary, and are discussed in greater detail with respect to FIGS. 3A, 3B, and 4A-4I. Additionally, in some embodiments, the phenyl group is replaced by another alkyl substituent (e.g., methyl, ethyl, propyl, isopropyl, etc.). The syntheses of the phosphorus-based flame-retardant molecules 240 are discussed with regard to FIGS. 3A and 3B. The phosphorus-based flame-retardant molecules 240 are reacted with the vanillin derivatives 215, 225, and 235 to form flame-retardant vanillin-derived molecules 104. These reactions are discussed in greater detail with regard to FIGS. 4A, 4D, and 4G.

Figure 3A:
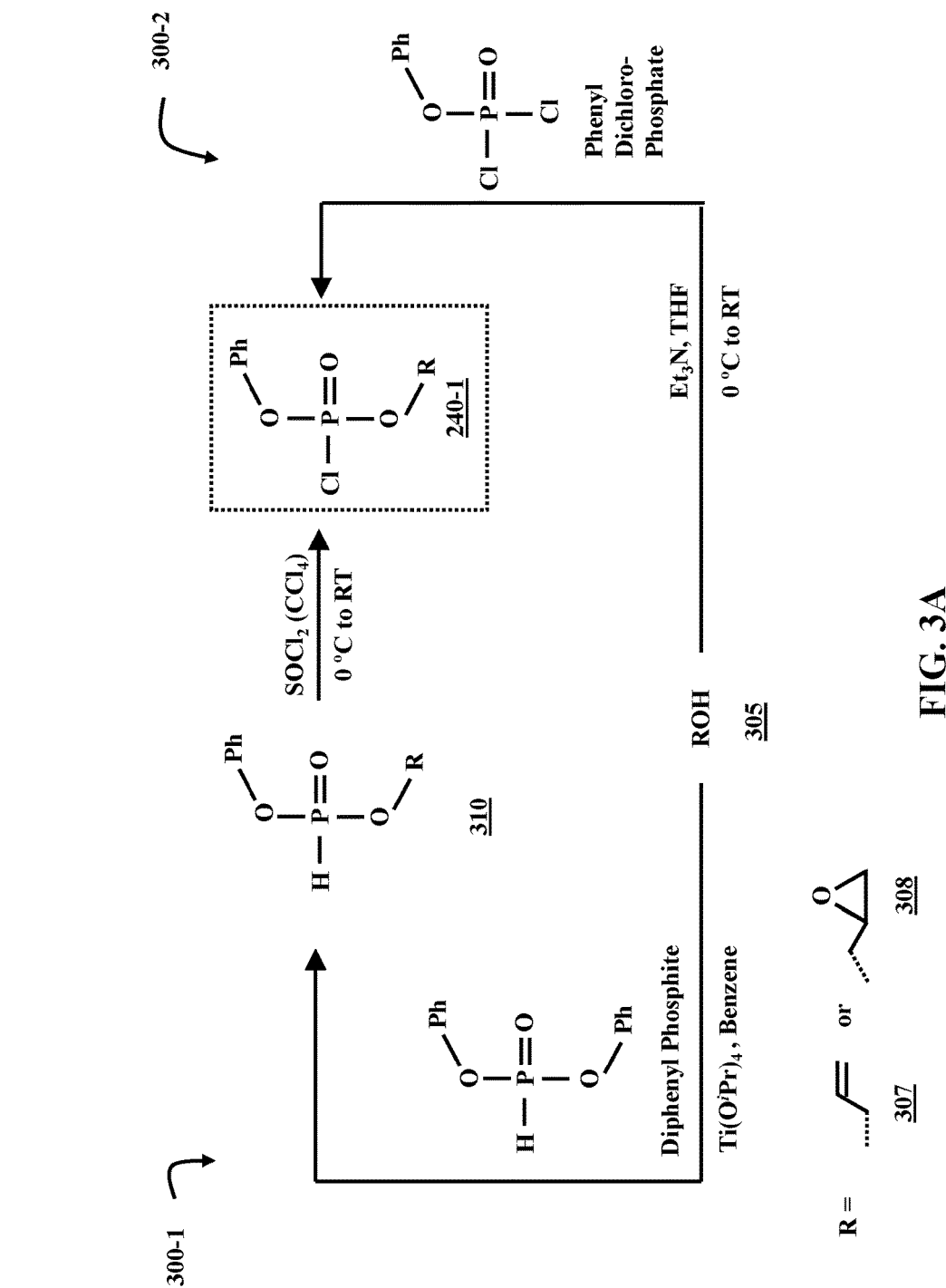
FIG. 3A is a chemical reaction diagram illustrating two processes of synthesizing the phosphate-based flame-retardant molecule, according to embodiments of the present disclosure.

FIG. 3A is a chemical reaction diagram illustrating two processes 300-1 and 300-2 of synthesizing the phosphate-based flame-retardant molecule 240-1, according to embodiments of the present disclosure. In both processes 300-1 and 300-2, an alcohol 305 is a starting material for the phosphate-based flame-retardant molecule 240-1. The alcohol 305 has either an allyl R group 307 or an epoxide R group 308. It should be noted that, though an allyl group 307 with a single methylene spacer group is illustrated here, other alcohols with allylic chains of varying lengths (e.g., one to twelve methylene spacer groups) could be used. Additionally, alcohols with acrylate substituents are used in some embodiments.

In process 300-1, the alcohol 305 is reacted with diphenyl phosphite and titanium isopropoxide (Ti(O$^i$Pr)$_4$) in benzene to produce a precursor 310 to the phosphate-based flame-retardant molecule 240-1. In this pseudo-transesterification reaction, the precursor 310 is formed when a phenyl (Ph) substituent on diphenyl phosphite is replaced by an allyl 307 or epoxide 308 R group from the alcohol 305. The precursor 310 is then reacted with thionyl chloride (SOCl$_2$) and carbon tetrachloride (CCl$_4$) over a range of 0° C. to room temperature (RT), forming the phosphate-based flame-retardant molecule 240-1.

In process 300-2, the alcohol 305 is reacted with phenyl dichlorophosphate in a tetrahydrofuran (THF) solution containing triethyl amine (Et$_3$N). This process is carried out over a range of 0° C. to room temperature (RT). A chloride on the phenyl dichlorophosphate is replaced by the alcohol 305, forming the phosphate-based flame-retardant molecule 240-1 with an allyl 307 or epoxide 308 R group.

Figure 3B:
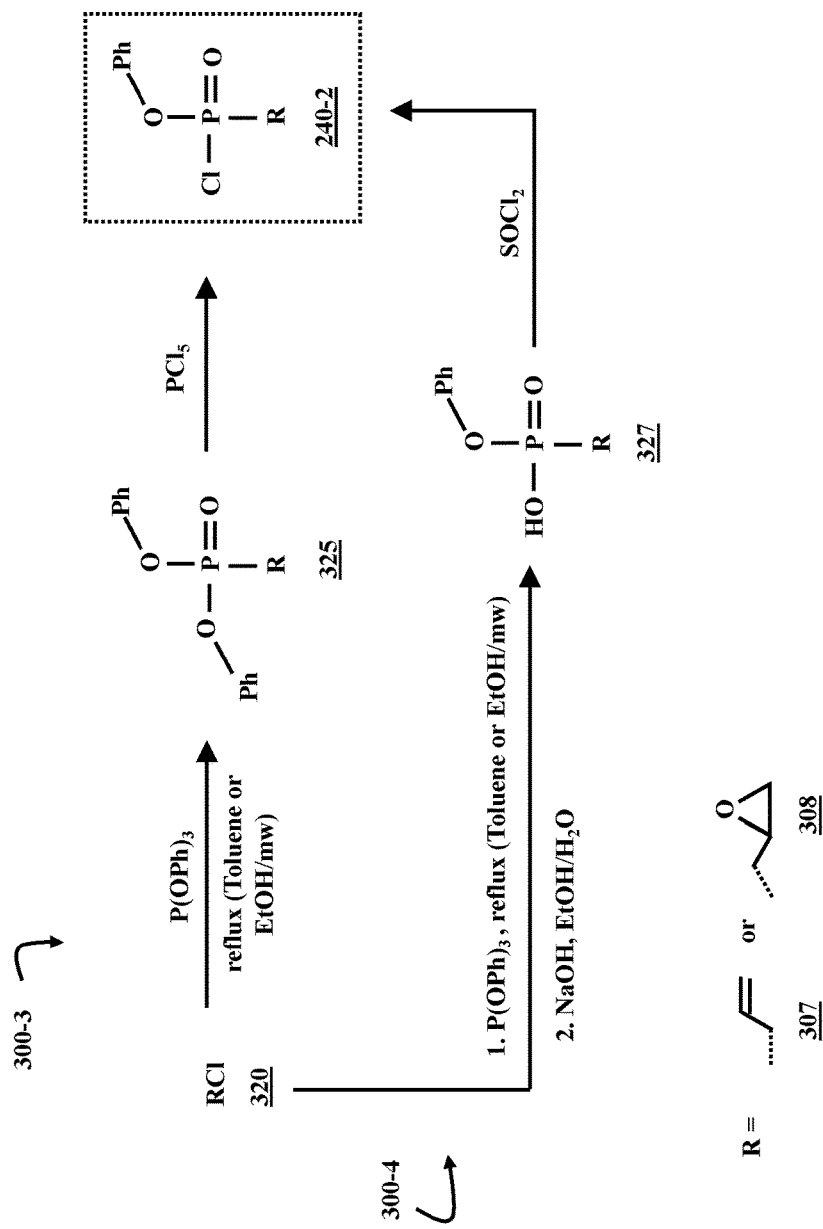
FIG. 3B is a chemical reaction diagram illustrating two processes of synthesizing the phosphonate-based flame-retardant molecule, according to embodiments of the present disclosure.

FIG. 3B is a chemical reaction diagram illustrating two processes 300-3 and 300-4 of synthesizing the phosphonate-based flame-retardant molecule 240-2, according to embodiments of the present disclosure. In both processes 300-3 and 300-4, an organochloride 320 is a starting material for the phosphonate-based flame-retardant molecule 240-2. The organochloride has either an allyl R group 307 or an epoxide R group 308. It should be noted that, as in the case of the alcohol 305, other organochlorides with allylic chains of varying lengths (e.g., one to twelve methylene spacer groups) could be used. Additionally, organochlorides with acrylate substituents are used in some embodiments.

In process 300-3, the organochloride 320 is reacted with triphenyl phosphite (P(OPh)$_3$). The mixture is heated, either by refluxing in toluene or microwaving (mw) in ethanol (EtOH), producing a phosphonyl ester precursor 325 to the phosphonate-based flame-retardant molecule 240-2. The phosphonyl ester precursor 325 is reacted with phosphorus pentachloride (PCl$_5$) to form the phosphonate-based flame-retardant molecule 240-2 with an allyl 307 or epoxide 308 R group.

In process 300-4, a mixture of the organochloride 320 and triphenyl phosphite (P(OPh)$_3$) is heated, either by refluxing in toluene or microwaving (mw) in ethanol (EtOH), forming a phenylphosphinic acid precursor 327 to the phosphonate-based flame-retardant molecule 240-2. The reaction is then quenched by raising the pH of the solution. In this prophetic example, an ethanol (EtOH)/water (H$_2$O) solution of sodium hydroxide (NaOH) is added to the reaction mixture. However, in some embodiments, bases other than sodium hydroxide, such as potassium hydroxide or lithium hydroxide, are used to quench the reaction. When the reaction has been quenched, thionyl chloride (SOCl$_2$) is added to the phenylphosphinic acid precursor 327, producing the phosphonate-based flame-retardant molecule 240-2 with an allyl 307 or epoxide 308 R group.

Figure 3C:
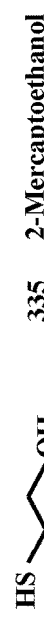
FIG. 3C is a diagrammatic representation of the molecular structures of three thiol molecules that are involved in the synthesis of the flame-retardant vanillin-derived molecules, according to some embodiments of the present disclosure.
Figure 3C:
Figure 3C:
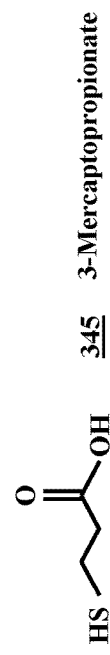
Figure 3C:
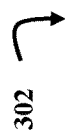

FIG. 3C is a diagrammatic representation of the molecular structures 302 of three thiol molecules that are involved in the synthesis of the flame-retardant vanillin-derived molecules, according to some embodiments of the present disclosure. The three thiol molecules are 2-mercaptoethanol 335, cysteamine hydrochloride (HCl) 340, and 3-mercaptopropionate 345. Each of these thiols is involved in the synthesis of a thioether-linked flame-retardant vanillin derivative. The thiol molecules provide a thioether R group. Details of the syntheses and structures of the thioether-linked flame-retardant vanillin derivatives are discussed in greater detail with regard to FIGS. 4B, 4E, and 4H.

Figure 4A:
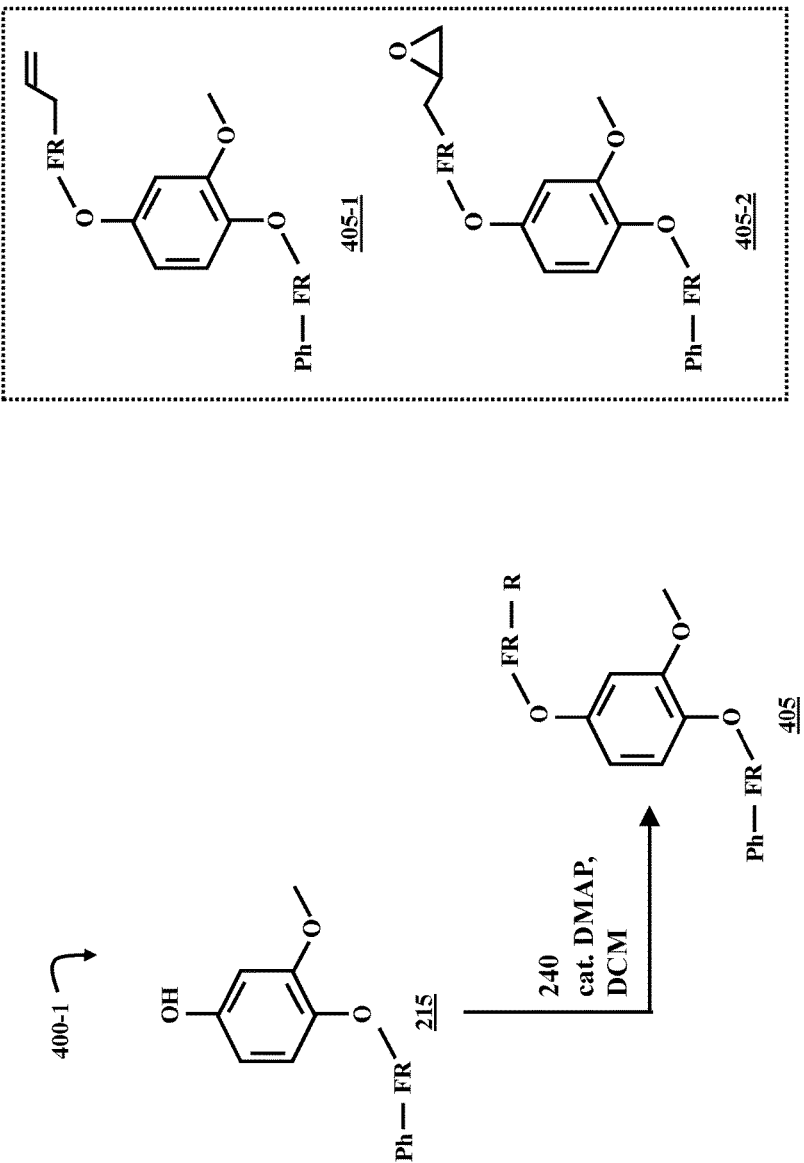
FIG. 4A is a chemical reaction diagram illustrating a process of synthesizing a functionalized flame-retardant phenol vanillin-derived molecule, according to some embodiments of the present disclosure.

FIG. 4A is a chemical reaction diagram illustrating a process 400-1 of synthesizing a functionalized flame-retardant phenol vanillin-derived molecule 405, according to some embodiments of the present disclosure. In process 400-1, the phenol flame-retardant derivative 215 of vanillin is reacted with a phosphorus-based flame-retardant molecule 240 and catalytic dimethylaminopyridine (DMAP) in a dichloromethane (DCM) solution. In some embodiments, stoichiometric triethylamine is used instead of DMAP. Stirring this mixture yields the functionalized flame-retardant phenol vanillin-derived molecule 405.

If process 400-1 is carried out with a phosphorus-based flame-retardant molecule 240 having an allyl R group 307, the functionalized flame-retardant phenol vanillin-derived molecule 405 will be an allyl-functionalized flame-retardant phenol vanillin-derived molecule 405-1. Likewise, if process 400-1 is carried out with a phosphorus-based flame-retardant molecule 240 having an epoxide R group 308, the functionalized flame-retardant phenol vanillin-derived molecule 405 will be an epoxide-substituted flame-retardant phenol vanillin-derived molecule 405-2. If the process is carried out with the phosphate-based flame-retardant molecule 240-1, the functionalized flame-retardant phenol vanillin-derived molecule 405 will have a phosphoryl FR group, and, if the reaction is carried out with the phosphonate-based flame-retardant molecule 240-2, the functionalized flame-retardant phenol vanillin-derived molecule 405 will have a phosphonyl FR group.

Figure 4B:
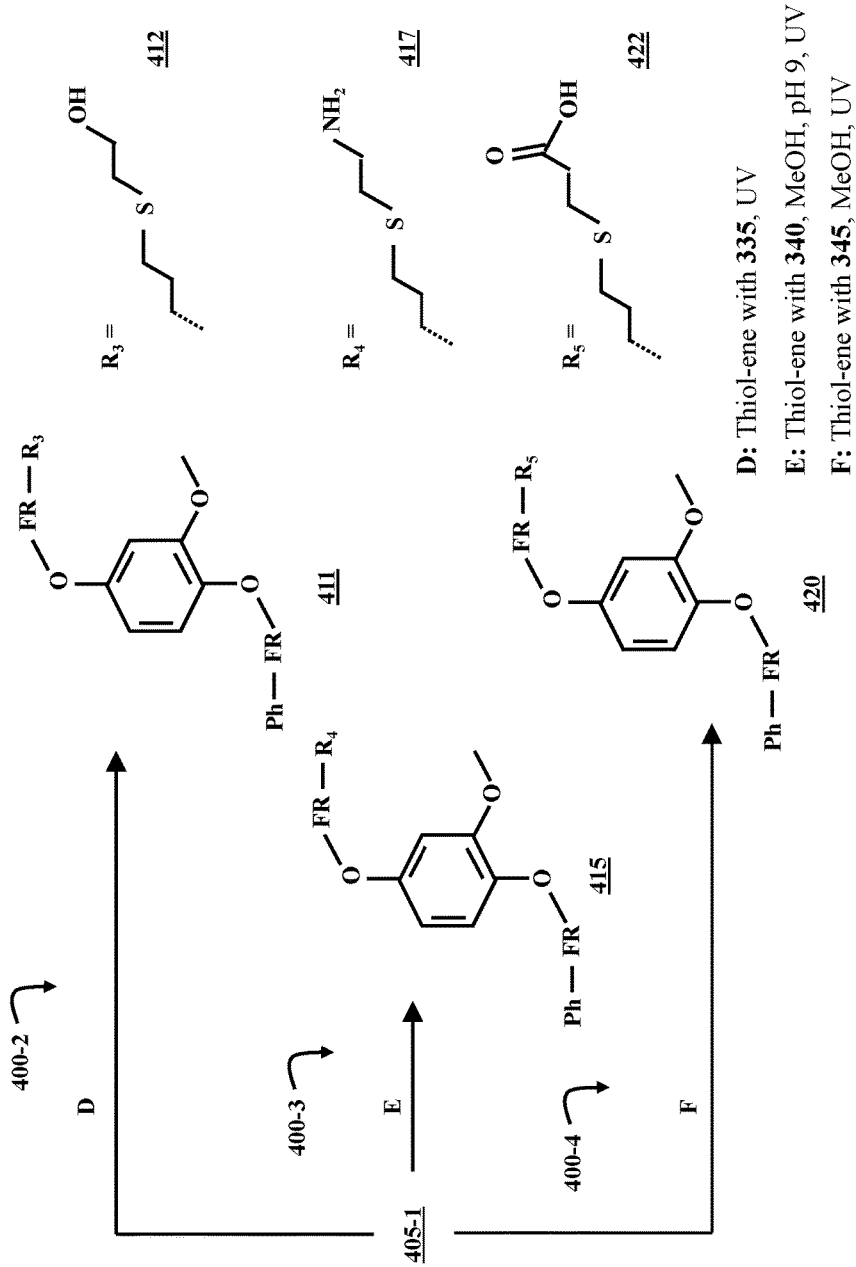
FIG. 4B is a chemical reaction diagram illustrating three processes of synthesizing thioether-linked flame-retardant phenol vanillin-derived molecules, according to some embodiments of the present disclosure.

FIG. 4B is a chemical reaction diagram illustrating three processes 400-2, 400-3, and 400-4 of synthesizing thioether-linked flame-retardant phenol vanillin-derived molecules, according to some embodiments of the present disclosure. Each process is a thiol-ene reaction between the allyl-functionalized flame-retardant phenol vanillin-derived molecule 405-1 and a thiol molecule. The thiol molecules used in processes 400-2, 400-3, and 400-4 are 2-mercaptoethanol 335, cysteamine HCl 340, and 3-mercaptopropionate 345, respectively. The structures of these thiol molecules are illustrated in FIG. 3C.

In process 400-2, the allyl-functionalized flame-retardant phenol vanillin-derived molecule 405-1 is reacted with 2-mercaptoethanol 335 under UV light. The resulting hydroxyl-functionalized flame-retardant phenol vanillin-derived molecule 410 has a thioether $R_3$ group 412 that corresponds to 2-mercaptoethanol 335. In process 400-3, the allyl-functionalized flame-retardant phenol vanillin-derived molecule 405-1 is reacted with cysteamine HCl 340 in a pH 9 methanol (MeOH) solution under UV light. The resulting amino-functionalized flame-retardant phenol vanillin-derived molecule 415 has a thioether $R_4$ group 417 that corresponds to cysteamine HCl 340. In process 400-4, the allyl-functionalized flame-retardant phenol vanillin-derived molecule 405-1 is reacted with 3-mercaptopropionate 345 under UV light in a methanol (MeOH) solution. The resulting carboxylic-acid functionalized flame-retardant phenol vanillin-derived molecule 420 has a thioether $R_5$ group 422 that corresponds to 3-mercaptopropionate 345.

Figure 4C:
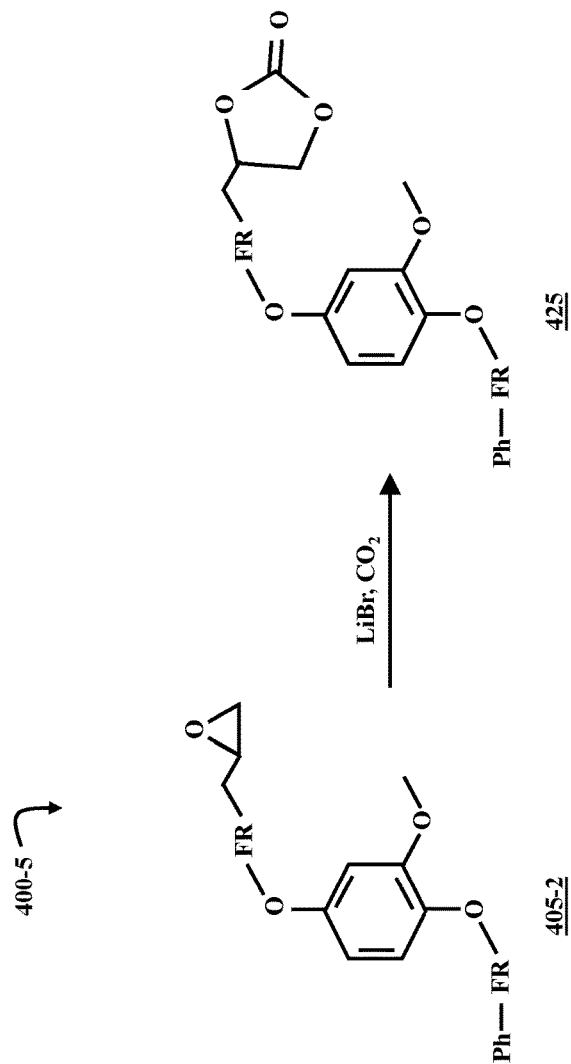
FIG. 4C is a chemical reaction diagram illustrating a process of synthesizing a propylene carbonate-functionalized flame-retardant phenol vanillin-derived molecule, according to some embodiments of the present disclosure.

FIG. 4C is a chemical reaction diagram illustrating a process 400-5 of synthesizing a propylene carbonate-functionalized flame-retardant phenol vanillin-derived molecule 425, according to some embodiments of the present disclosure. The epoxide-functionalized flame-retardant phenol vanillin-derived molecule 405-2 is combined with lithium bromide (LiBr). Carbon dioxide ($CO_2$) is added to the mixture, either by injecting it into the headspace of the reaction flask, or by bubbling it through the solution. This step yields the propylene carbonate-functionalized flame-retardant phenol vanillin-derived molecule 425.

Figure 4D:
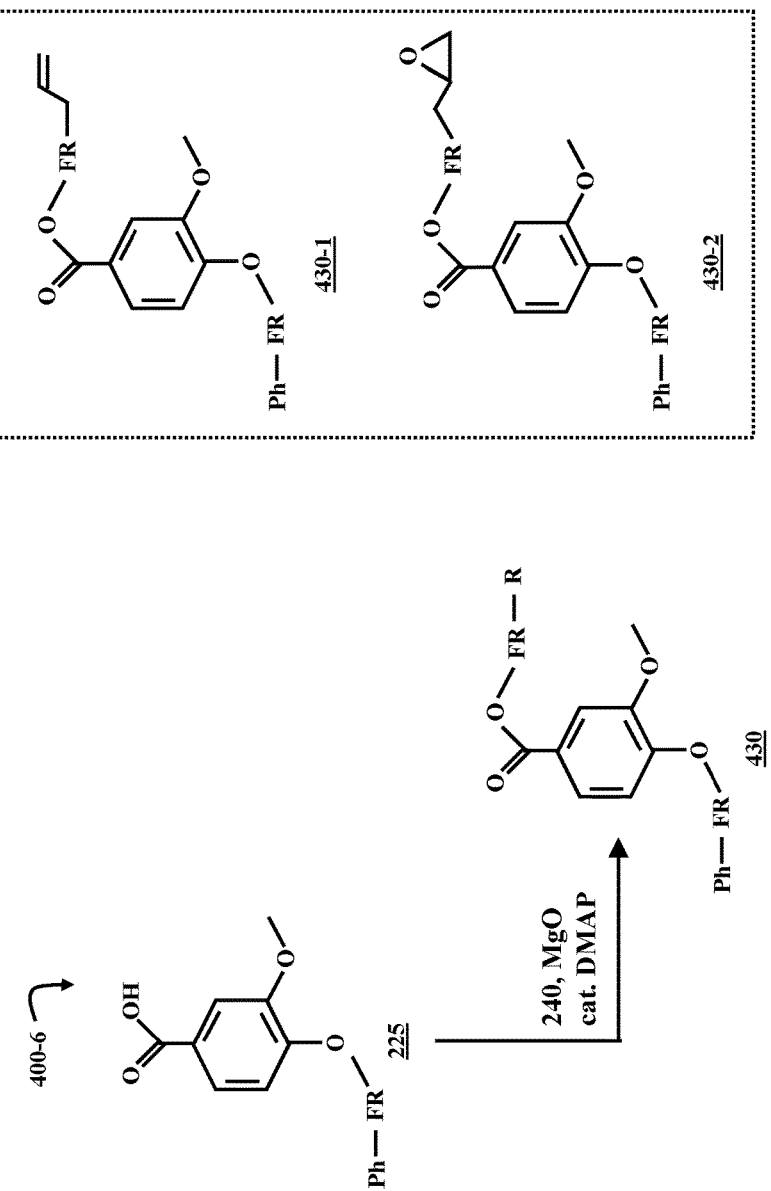
FIG. 4D is a chemical reaction diagram illustrating a process of synthesizing a functionalized flame-retardant carboxylic acid vanillin-derived molecule, according to some embodiments of the present disclosure.

FIG. 4D is a chemical reaction diagram illustrating a process 400-6 of synthesizing a functionalized flame-retardant carboxylic acid vanillin-derived molecule 430, according to some embodiments of the present disclosure. The carboxylic acid flame-retardant derivative 225 of vanillin is reacted with a phosphorus-based flame-retardant molecule 240, as well as magnesium oxide (MgO) and catalytic dimethylaminopyridine (DMAP). In some embodiments, DMAP is omitted from the reaction. Stirring this mixture yields the functionalized flame-retardant carboxylic acid vanillin-derived molecule 430.

If process 400-6 is carried out with a phosphorus-based flame-retardant molecule 240 having an allyl R group 307, the functionalized carboxylic acid vanillin-derived molecule 430 will be an allyl-functionalized flame-retardant carboxylic acid vanillin-derived molecule 430-1. Likewise, if process 400-6 is carried out with a phosphorus-based flame-retardant molecule 240 having an epoxide R group 308, the functionalized carboxylic acid vanillin-derived molecule 430 will be an epoxide-substituted flame-retardant carboxylic acid vanillin-derived molecule 430-2. If the process is carried out with the phosphate-based flame-retardant molecule 240-1, the functionalized flame-retardant carboxylic acid vanillin-derived molecule 430 will have a phosphoryl FR group, and, if the reaction is carried out with the phosphonate-based flame-retardant molecule 240-2, the functionalized flame-retardant carboxylic acid vanillin-derived molecule 430 will have a phosphonyl FR group.

Figure 4E:
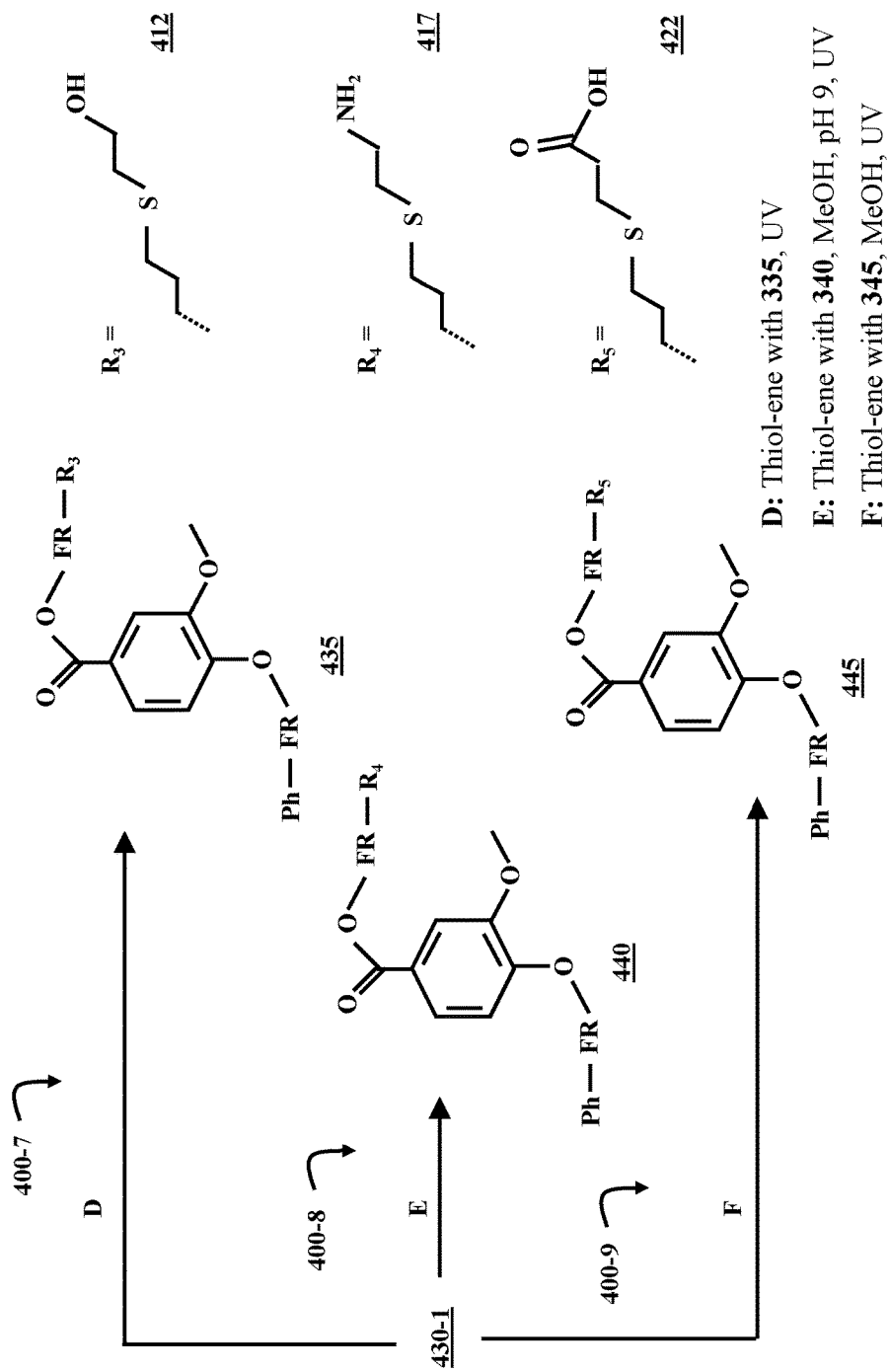
FIG. 4E is a chemical reaction diagram illustrating three processes of synthesizing thioether-linked flame-retardant carboxylic acid vanillin-derived molecules, according to some embodiments of the present disclosure.

FIG. 4E is a chemical reaction diagram illustrating three processes 400-7, 400-8, and 400-9 of synthesizing thioether-linked flame-retardant carboxylic acid vanillin-derived molecules, according to some embodiments of the present disclosure. Each process is a thiol-ene reaction between the allyl-functionalized flame-retardant carboxylic acid vanillin-derived molecule 430-1 and a thiol molecule. The thiol molecules used in processes 400-7, 400-8, and 400-9 are 2-mercaptoethanol 335, cysteamine HCl 340, and 3-mercaptopropionate 345, respectively. The structures of these thiol molecules are illustrated in FIG. 3C.

In process 400-7, the allyl-functionalized flame-retardant carboxylic acid vanillin-derived molecule 430-1 is reacted with 2-mercaptoethanol 335 under UV light. The resulting hydroxyl-functionalized flame-retardant carboxylic acid vanillin-derived molecule 435 has a thioether $R_3$ group 412 that corresponds to 2-mercaptoethanol 335. In process 400-8, the allyl-functionalized flame-retardant carboxylic acid vanillin-derived molecule 430-1 is reacted with cysteamine HCl 340 in a pH 9 methanol (MeOH) solution under UV light. The resulting amino-functionalized flame-retardant carboxylic acid vanillin-derived molecule 440 has a thioether $R_4$ group 417 that corresponds to cysteamine HCl 340. In process 400-9, the allyl-functionalized flame-retardant carboxylic acid vanillin-derived molecule 430-1 is reacted with 3-mercaptopropionate 345 under UV light in a methanol (MeOH) solution. The resulting carboxylic-acid functionalized flame-retardant carboxylic acid vanillin-derived molecule 445 has a thioether $R_5$ group 422 that corresponds to 3-mercaptopropionate 345.

Figure 4F:
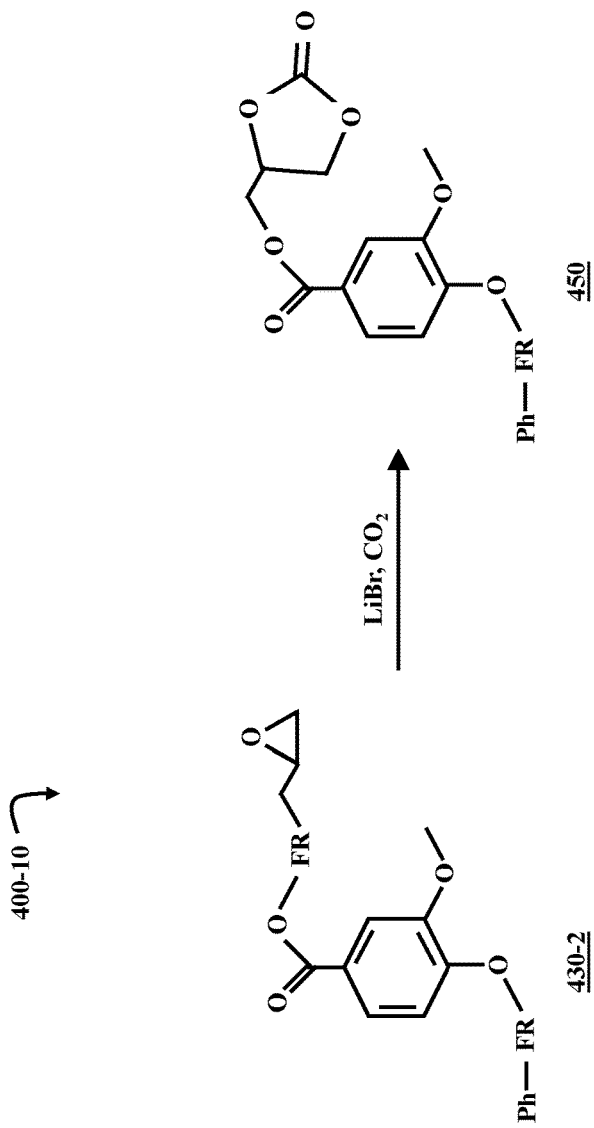
FIG. 4F is a chemical reaction diagram illustrating a process of synthesizing a propylene carbonate-functionalized flame-retardant carboxylic acid vanillin-derived molecule, according to some embodiments of the present disclosure.

FIG. 4F is a chemical reaction diagram illustrating a process 400-10 of synthesizing a propylene carbonate-functionalized flame-retardant carboxylic acid vanillin-derived molecule 450, according to some embodiments of the present disclosure. The epoxide-functionalized flame-retardant carboxylic acid vanillin-derived molecule 430-2 is combined with lithium bromide (LiBr). Carbon dioxide ($CO_2$) is added to the mixture, either by injecting into the headspace of the reaction flask, or by bubbling through the solution. The step yields the propylene carbonate-functionalized flame-retardant carboxylic acid vanillin-derived molecule 450.

Figure 4G:
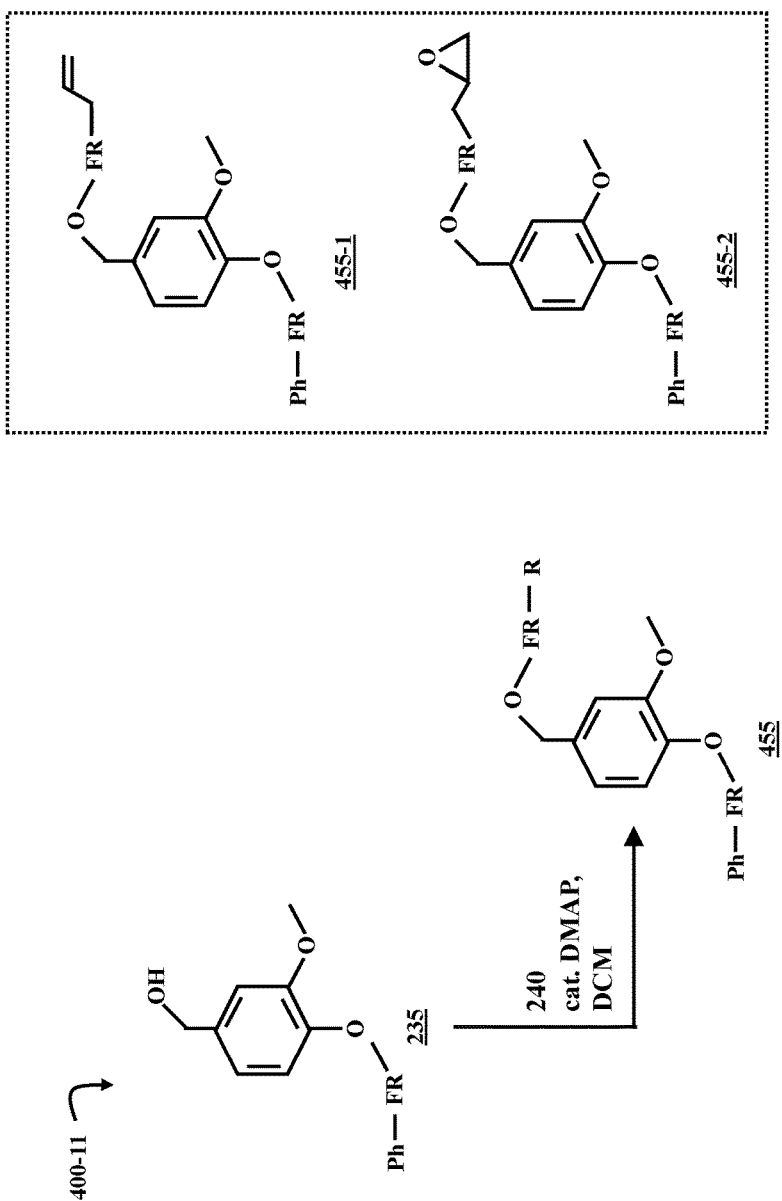
FIG. 4G is a chemical reaction diagram illustrating a process of synthesizing a functionalized flame-retardant benzyl alcohol vanillin-derived molecule, according to some embodiments of the present disclosure.

FIG. 4G is a chemical reaction diagram illustrating a process 400-11 of synthesizing a functionalized flame-retardant benzyl alcohol vanillin-derived molecule 455, according to some embodiments of the present disclosure. The benzyl alcohol flame-retardant derivative 235 of vanillin is reacted with a phosphorus-based flame-retardant molecule 240 and catalytic dimethylaminopyridine (DMAP) in a dichloromethane (DCM) solution. In some embodiments, stoichiometric triethylamine is used instead of DMAP. Stirring this mixture yields the functionalized flame-retardant benzyl alcohol vanillin-derived molecule 455.

If process 400-11 is carried out with a phosphorus-based flame-retardant molecule 240 having an allyl R group 307, the functionalized benzyl alcohol vanillin-derived molecule 455 will be an allyl-functionalized flame-retardant benzyl alcohol vanillin-derived molecule 455-1. Likewise, if process 400-11 is carried out with a phosphorus-based flame-retardant molecule 240 having an epoxide R group 308, the functionalized benzyl alcohol vanillin-derived molecule 455 will be an epoxide-substituted flame-retardant benzyl alcohol vanillin-derived molecule 455-2. If the process is carried out with the phosphate-based flame-retardant molecule 240-1, the functionalized flame-retardant benzyl alcohol vanillin-derived molecule 455 will have a phosphoryl FR group, and, if the reaction is carried out with the phosphonate-based flame-retardant molecule 240-2, the functionalized flame-retardant benzyl alcohol vanillin-derived molecule 455 will have a phosphonyl FR group.

Figure 4H:
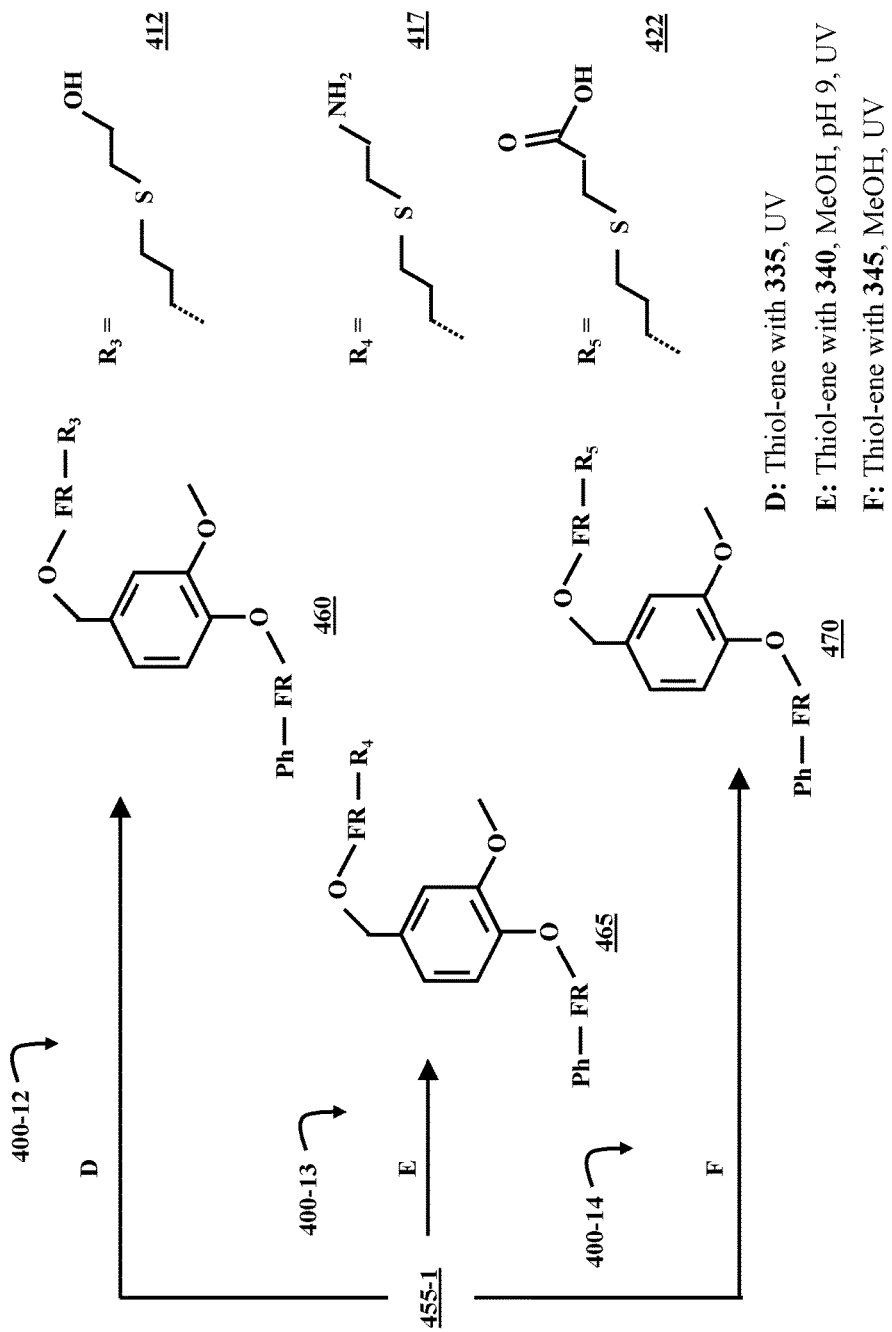
FIG. 4H is a chemical reaction diagram illustrating three processes of synthesizing thioether-linked flame-retardant benzyl alcohol vanillin-derived molecules, according to some embodiments of the present disclosure.

FIG. 4H is a chemical reaction diagram illustrating three processes 400-12, 400-13, and 400-14 of synthesizing thioether-linked flame-retardant benzyl alcohol vanillin-derived molecules, according to some embodiments of the present disclosure. Each process is a thiol-ene reaction between the allyl-functionalized flame-retardant benzyl alcohol vanillin-derived molecule 455-1 and a thiol molecule. The thiol molecules used in processes 400-12, 400-13, and 400-14 are 2-mercaptoethanol 335, cysteamine HCl 340, and 3-mercaptopropionate 345, respectively. The structures of these thiol molecules are illustrated in FIG. 3C.

In process 400-12, the allyl-functionalized flame-retardant benzyl alcohol vanillin-derived molecule 455-1 is reacted with 2-mercaptoethanol 335 under UV light. The resulting hydroxyl-functionalized flame-retardant benzyl alcohol vanillin-derived molecule 460 has a thioether $R_3$ group 412 that corresponds to 2-mercaptoethanol 335. In process 400-13, the allyl-functionalized flame-retardant benzyl alcohol vanillin-derived molecule 455-1 is reacted with cysteamine HCl 340 in a pH 9 methanol (MeOH) solution under UV light. The resulting amino-functionalized flame-retardant benzyl alcohol vanillin-derived molecule 465 has a thioether $R_4$ group 417 that corresponds to cysteamine HCl 340. In process 400-14, the allyl-functionalized flame-retardant carboxylic acid vanillin-derived molecule 455-1 is reacted with 3-mercaptopropionate 345 under UV light in a methanol (MeOH) solution. The resulting carboxylic-acid functionalized flame-retardant benzyl alcohol vanillin-derived molecule 470 has a thioether $R_5$ group 422 that corresponds to 3-mercaptopropionate 345.

Figure 4I:
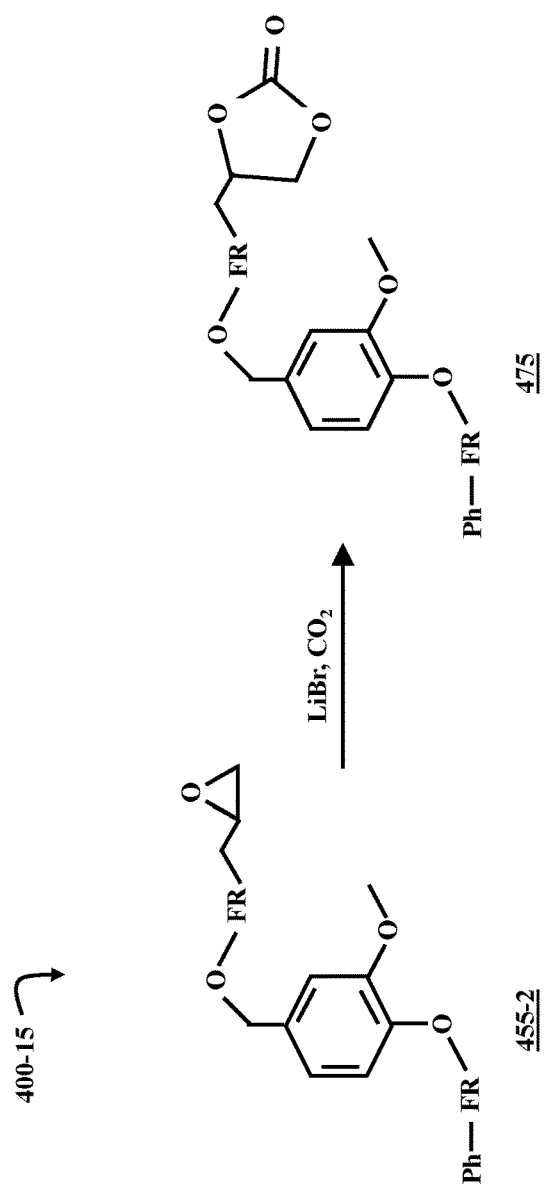
FIG. 4I is a chemical reaction diagram illustrating a process of synthesizing a propylene carbonate-functionalized flame-retardant benzyl alcohol vanillin-derived molecule, according to some embodiments of the present disclosure.

FIG. 4I is a chemical reaction diagram illustrating a process 400-15 of synthesizing a propylene carbonate-functionalized flame-retardant benzyl alcohol vanillin-derived molecule 475, according to some embodiments of the present disclosure. The epoxide-functionalized flame-retardant benzyl alcohol vanillin-derived molecule 455-2 is combined with lithium bromide (LiBr). Carbon dioxide ($CO_2$) is added to the mixture, either by injecting into the headspace of the reaction flask, or by bubbling through the solution. The reaction yields the propylene carbonate-functionalized flame-retardant benzyl alcohol vanillin-derived molecule 475.

In some embodiments, the processes of forming substituted flame-retardant vanillin derivatives illustrated in FIGS. 4A, 4D, and 4G are carried out with a mixture of both the phosphate-based 240-1 and the phosphonate-based 240-2 flame retardant molecules. Carrying out processes 400-1, 400-6, and 400-11 with a mixture of the phosphate-240-1 and phosphonate-based 240-2 flame retardant molecules can result in substituted flame-retardant vanillin derivatives with both phosphoryl and phosphonyl FR groups. However, in some instances, adding a mixture of phosphate-240-1 and phosphonate-based 240-2 flame retardant molecules can result in the production of substituted flame-retardant vanillin derivatives with all phosphoryl or all phosphonyl FR groups. Additionally, adding both phosphate-240-1 and phosphonate-based 240-2 flame retardant molecules to the reaction can yield a mixture of products that includes some combination of derivatives with either all phosphoryl or all phosphonyl FR groups and derivatives with both phosphoryl and phosphonyl FR groups.

The flame-retardant vanillin-derived molecules 104 disclosed herein can be bound to resins via their R functional groups, imparting flame-retardant properties to the resins. Additionally, the resins can be polymerized, or used without polymerization in applications such as varnishes and adhesives. The polymers formed from the resins are also flame-retardant, due to the presence of the bound flame-retardant vanillin-derived molecules 104. The flame-retardant polymers and resins can be used in a number of devices.

One example of a polymer that can be made flame-retardant by the addition of flame-retardant vanillin-derived molecules 104 is polycarbonate-acrylonitrile butadiene styrene (PC-ABS), a plastic that is often used in electronics hardware. Flame-retardant vanillin-derived molecules 104 can also be incorporated into polyurethane. Polyurethane is a versatile polymer used in applications that can include acoustic dampening, cushioning, plastics, synthetic fibers, insulation, adhesives, etc. The flame-retardant vanillin-derived molecules 104 can also be added to adhesives such as bio-adhesives, elastomers, thermoplastics, emulsions, thermosets, etc. Further, materials containing the flame-retardant vanillin-derived molecules 104 can be incorporated into various devices with electronic components that can include printed circuit boards (PCBs), semiconductors, transistors, optoelectronics, capacitors, resistors, etc.

Resins for printed circuit boards (PCBs) can be made flame-retardant by incorporating flame-retardant vanillin-derived molecules 104. PCBs are electrical circuits that can be found in most types of electronic device, and they support and electronically connect electrical components in the device. PCBs are formed by etching a copper conductive layer laminated onto an insulating substrate. The insulating substrate can be a laminate comprising a resin and a fiber. Many resins in PCBs contain a polymer, such as an epoxy, a polyurethane, a polyhydroxyurethane, a polycarbonate, a polyester, a polyacrylate, a polyimide, a polyamide, a polyurea, a poly(vinyl-ester), etc. Flame-retardant vanillin-derived vanillin molecules 104 can be bound to the polymers in the PCB resin in order to prevent the PCB from catching fire when exposed to high temperature environments or electrical power overloads.

It should be noted that, in some embodiments, the compounds described herein can contain one or more chiral centers. These can include racemic mixtures, diastereomers, enantiomers, and mixtures containing one or more stereoisomer. Further, the disclosed can encompass racemic forms of the compounds in addition to individual stereoisomers, as well as mixtures containing any of these.

The synthetic processes discussed herein and their accompanying drawings are prophetic examples, and are not limiting; they can vary in reaction conditions, components, methods, etc. In addition, the reaction conditions can optionally be changed over the course of a process. In some instances, reactions that involve multiple steps can be carried out sequentially, and, in other instances, they can be carried out in one pot. Further, in some embodiments, processes can be added or omitted while still remaining within the scope of the disclosure, as will be understood by a person of ordinary skill in the art.

What is claimed is:

1. A bondable flame-retardant vanillin-derived molecule with a formula of:

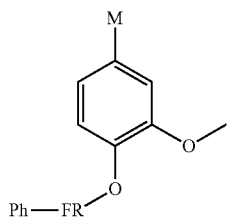

wherein M is a flame-retardant substituent; and
wherein FR is a phosphorus-based moiety.

2. The flame-retardant vanillin-derived molecule of claim 1, wherein the M is selected from a group consisting of substituents with formulas of:

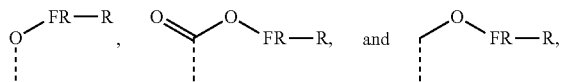

wherein FR is a second phosphorus-based moiety; and
wherein R is a substituent selected from a group consisting of an allyl substituent, an epoxide substituent, a propylene carbonate substituent, and a thioether substituent.

3. The flame-retardant vanillin-derived molecule of claim 1, wherein the FR is a phosphoryl moiety with a formula of:

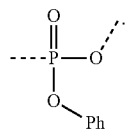

4. The flame-retardant vanillin-derived molecule of claim 1, wherein the FR is a phosphonyl moiety with a formula of:

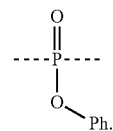

5. The flame-retardant vanillin-derived molecule of claim 2, wherein the thioether substituent is selected from a group consisting of a hydroxyl-functionalized thioether substituent, an amino-functionalized thioether substituent, and a carboxylic acid-functionalized thioether substituent.

6. The flame-retardant vanillin-derived molecule of claim 1, wherein the flame-retardant vanillin-derived molecule is bound to a resin.

7. The flame-retardant vanillin-derived molecule of claim 1, wherein the flame-retardant vanillin-derived molecule is bound to a polymer.

* * * * *